US008968751B2

(12) United States Patent
Saurat et al.

(10) Patent No.: US 8,968,751 B2
(45) Date of Patent: Mar. 3, 2015

(54) TOPICAL COMPOSITIONS ASSOCIATING SODIUM HYALURONATE FRAGMENTS AND RETINOID USEFUL FOR COSMETIC AND MEDICAL DERMATOLOGY

(75) Inventors: Jean-Hilaire Saurat, Geneva (CH); Gürkan Kaya, Geneva (CH); Pascal Bordat, Mervilla (FR)

(73) Assignee: Pierre Fabre Dermo Cosmetique, Boulogne-Billancourt (FR)

( * ) Notice: Subject to any disclaimer, the term of this patent is extended or adjusted under 35 U.S.C. 154(b) by 913 days.

(21) Appl. No.: 10/587,652

(22) PCT Filed: Jan. 27, 2005

(86) PCT No.: PCT/FR2005/000176
§ 371 (c)(1),
(2), (4) Date: Sep. 29, 2006

(87) PCT Pub. No.: WO2005/082327
PCT Pub. Date: Sep. 9, 2005

(65) Prior Publication Data
US 2007/0172442 A1     Jul. 26, 2007

(30) Foreign Application Priority Data

Jan. 29, 2004   (FR) ...................................... 0400826

(51) Int. Cl.
| A61K 31/728 | (2006.01) |
| A61K 8/73 | (2006.01) |
| A61K 8/67 | (2006.01) |
| A61K 31/74 | (2006.01) |
| A61Q 19/00 | (2006.01) |
| A61Q 19/08 | (2006.01) |

(52) U.S. Cl.
CPC ................. *A61K 8/735* (2013.01); *A61K 8/671* (2013.01); *A61K 31/74* (2013.01); *A61Q 19/00* (2013.01); *A61Q 19/08* (2013.01)
USPC ........................... 424/400; 424/70.13; 514/54

(58) Field of Classification Search
USPC ..................................................... 424/70.13
See application file for complete search history.

(56) References Cited

U.S. PATENT DOCUMENTS

| 4,303,676 | A | * | 12/1981 | Balazs ........................... 514/773 |
| 5,977,088 | A | | 11/1999 | Harper et al. |
| 6,193,956 | B1 | * | 2/2001 | Liu et al. ........................ 424/45 |
| 6,426,081 | B1 | | 7/2002 | Chong |
| 2004/0197282 | A1 | | 10/2004 | Neudecker et al. |

FOREIGN PATENT DOCUMENTS

| EP | 0 138 572 A2 | 4/1985 |
| EP | 0138572 A2 | 4/1985 |
| EP | 0 197 718 A2 | 10/1986 |
| EP | 0610511 A1 | 8/1994 |
| EP | 1384482 A1 | 4/2004 |
| GB | 2 228 736 A | 9/1990 |
| JP | 62-502546 A | 10/1987 |
| JP | 64-40412 A | 2/1989 |
| JP | 6-32728 A | 2/1994 |
| JP | 2000-344656 A | 12/2000 |
| JP | 2002-284662 A | 10/2002 |
| WO | WO 86/06275 A1 | 11/1986 |
| WO | WO-91/04279 A1 | 4/1991 |
| WO | WO-93/16732 A1 | 9/1993 |
| WO | WO-00/38647 A1 | 7/2000 |
| WO | WO-01/03657 A1 | 1/2001 |
| WO | WO-2005/039532 A1 | 5/2005 |

OTHER PUBLICATIONS

Mitani et al., "Molecular Weights of Hyaluronic Acid and Mositurizing Effects", vol. 12, No. 1 (1988) pp. 50-59.
Database WPI, Section Ch, Week 200267, Derwent Publications Ltd., London, GB; AN 2001-430654, XP002330935.
McKee et al., J. Clin. Invest., vol. 98, No. 10, pp. 2403-2413, (Nov. 1996).
Brown et al., J. Invest. Dermatol., vol. 113, No. 5, pp. 740-746, (Nov. 1999).
Termeer et al., The Journal of Immunology, vol. 165, pp. 1863-1870, (2000).
Kaya et al., J. Invest. Dermatol., vol. 115, No. 6, pp. 1054-1058, (Dec. 2000).
Kaya et al., Genes & Development, vol. 11, pp. 996-1007, (1997).
Fitzgerald et al., The Journal of Immunology, vol. 164, pp. 2053-2063, (2000).
Saurat et al., Dermatologica, vol. 177, pp. 218-224, (1988).
K. Thestrup-Pedersen, British Journal of Dematology, vol. 118, pp. 811-818, (1988).
Kato et al., Biochem J., vol. 286, pp. 755-760, (1992).
Blomhoff et al., The American Physiological Society, vol. 71, No. 4, pp. 951-990, (Oct. 1991).
IUPAC-IUB Int. Comm. On Biochem. Nomenclature, Eur. J. Biochem., vol. 129, pp. 1-5, (1982).
Torvard C Laurent et al., Immunology and Cell Biology (1996) vol. 74, pp. A1-A7.
S.Burt Wolbach et al., J Exp.Med. 43: pp. 753-777, (1925).
English language translation of JP 2000-344656, Jun. 1, 1999, Kurimura et al.
Casado, F.J. et al., "LMW Hyaluronic Acid to Induce Epidermal Regeneration", Drug & Cosmetic Industry, 148(3), pp. 30, 32, 34 and 74, (Mar. 1991).
Japanese Office Action dated May 31, 2011.
Koizumi, H., "Special Review/Activation of Skin Cells and Cosmetic Development Keratinization Disorders and Retinoids", Fragrance Journal, 20(2), pp. 26-31, (1992).
Tholon, L. et al., "Encapsulation Technologies Applied to Retinoids, a Way to Modulate Bioavailability and Reactivity", Fragrance Journal, 29(2), pp. 83-90, (2001).

* cited by examiner

*Primary Examiner* — Brian-Yong Kwon
*Assistant Examiner* — Luke Karpinski
(74) *Attorney, Agent, or Firm* — Birch, Stewart, Kolasch & Birch, LLP

(57) ABSTRACT

The inventive compositions for topical application are characterized in that they comprises one or several hyaluronate fragments in the form of a main principle whose molecular weight ranges from 50 000 and 750 000 Da and a retinoid if necessary.

7 Claims, 1 Drawing Sheet

Figure 1: HA dosage in the epidermis
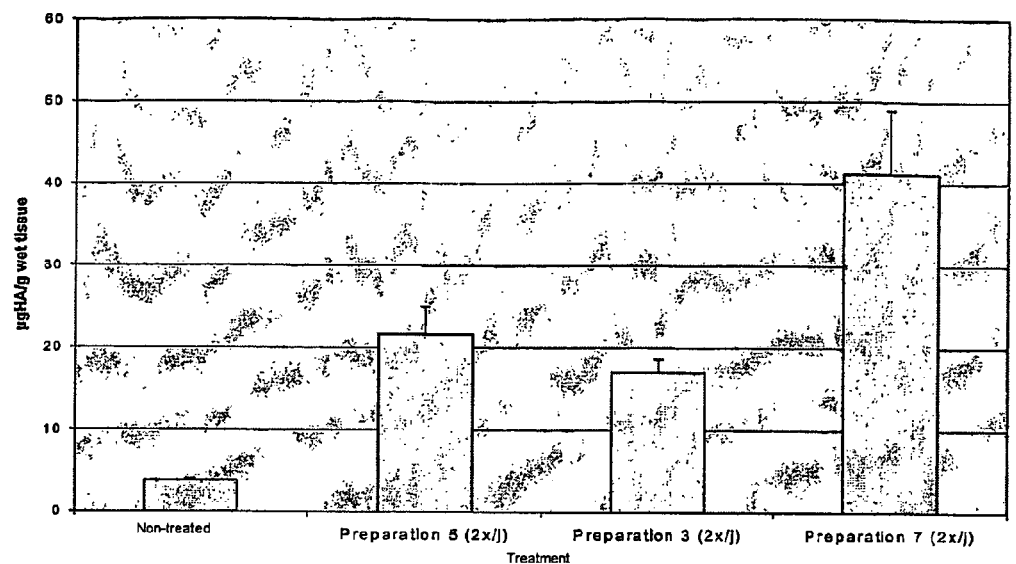
Figure 2: HA dosage in the dermis
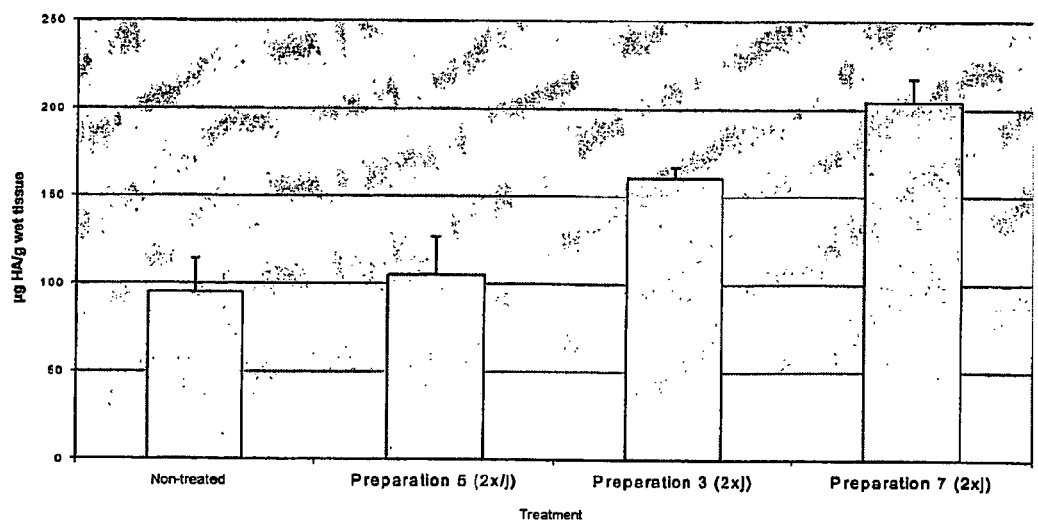

TOPICAL COMPOSITIONS ASSOCIATING SODIUM HYALURONATE FRAGMENTS AND RETINOID USEFUL FOR COSMETIC AND MEDICAL DERMATOLOGY

The present invention relates to hyaluronate-based topical compositions, their use in cosmetology and dermatology.

Hyaluronate (HA) is the major component of the extracellular matrix. It is especially present in so-called "soft" connective tissues as opposed to other glycosaminoglycans such as chondroitin sulfuric acid present in so-called "hard" tissues such as cartilage. It is thus again found in significant amounts mainly in the skin.

HA is a non-sulfated linear glycosaminoglycan consisting of recurrent units of D-glucuronic acid and N-acetyl-D-glucosamine (Tammi R., Agren U M., Tuhkanen A L., Tammi M. *Hyaluronan metabolism in skin. Progress in Histochemistry & Cytochemistry.* 29(2): 1-81, 1994).

In normal skin, HA is essentially synthesized by dermal fibroblast and epidermal keratinocytes (Tammi R., already cited). By means of these residues bearing a negative charge, HA plays the role of a water pump with which the elasticity of the skin may be maintained. HA has a main role in controlling diffusion of food stuffs, hormones, vitamins, and inorganic salts of the connective tissue and in cleaning metabolic waste which may induce inflammatory reactions. With age, the amount of HA and its degree of polymerization decrease, resulting in a reduction of the amount of water retained in the connective tissue. The skin then experiences an aging process which results in an increase of fibrosis and in a lowering of elastic fiber content.

In normal human skin, HA exists as a polymer with a high molecular weight (600,000-1,000,000 Da). Physiological degradation of HA in the skin occurs by (i) internalization by keratinocytes via CD44 and (ii) intracellular fragmentation into fragments of intermediate size by hyaluronidases (60,000-300,000 Da). Fragmented HA is released by the keratinocytes, passes through the basal membrane and is directly released in the lymphatic vessels (Tammi R. et al., already cited).

Under inflammatory conditions, accumulation of forms of HA with low molecular weight has been demonstrated in animals. During the inflammation, platelet chemotactic factors like fibrin stimulate the affluence and activation of fibroblasts which degrade HA by secretion of hyaluronidase resulting in high tissue concentrations of small HA fragments. The generation of these small HA fragments also occurs through different mechanisms such as depolymerization by oxygen-reactive species released by granulocytes, or in skin irradiated with ultraviolet rays, or de novo synthesis of low molecular weight fragments. Several studies have suggested that high and low molecular weight HA may have different biological effects on cells and tissues (McKee C M., Penno M B., Cowman M., Burdick M D., Strieter R M., Bao C., Noble P W. *Hyaluronan (HA) fragments induce chemokine gene expression in alveolar macrophages. The role of HA size and CD44. Journal of Clinical investigation.* 98(10): 2403-13, 1996: Termeer C C., Hennies J., Voith U., Ahrens T., Weiss J M., Prehm P., Simon J C. *Oligosaccharides of hyaluronan are potent activators of dendritic cells. Journal of Immunology.* 165(4): 1863-70, 2000; Fitzgerald K A., Bowie A G., Skeffington B S., O'Neil L A., *Ras, Protein kinase C zeta, and I kappa B kinases 1 and 2 are downstream effectors of CD44 during the activation of NF-kappa B by hyaluronic acid fragments in T-24 carcinoma cells. Journal of Immunology.* 164(4): 2053-63, 2000).

It was demonstrated that HA of intermediate molecular weights (50,000-250,000 Da), applied on murine and human skin, passes through the epidermal and dermal layers. The degradation products appear in serum, 2 hours after applying HA on the skin. The molecular weight of HA recovered in serum is slightly less than that of HA applied on the skin, thereby demonstrating that transcutaneous passage of HA is not only limited to fragments of smaller size (100-10,000 Da) (Brown T J., Alcorn D, Fraser J R. *Absorption of hyaluronan applied to the surface of intact skin. Journal of investigative Dermatology.* 113(5): 740-6, 1999).

Vitamin A (retinol) and its natural and synthetic derivatives, collectively designated as retinoids, form a large diversity of substances having pronounced effects notably in embryogenesis, reproduction, mechanism of vision, growth regulation and the phenomenon of cellular differentiation (Blomhoff R. et al. 1991, *Physiol. Rev.* 71: 951-990; Sporn M. B. et al. (1994) in *the Retinoids*, $2^{nd}$ Ed. Raven Press, NY).

Natural retinoids are defined by the following general formula (I) as defined in (IUPAC-IUB *Joint Commission on Biochemical Nomenclature in Eur. J. Biochem.* (1982), 129, 1-5):

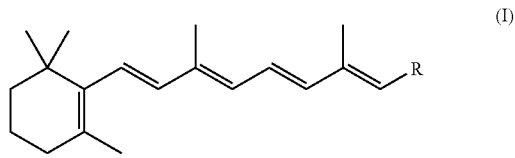

wherein R=$CH_2OH$ corresponds to retinol (ROL)
R=CHO corresponds to retinal (RAL)
R=COOH corresponds to retinoic acid (RA).

The biological effects of retinoids are mediated by their interaction with nuclear receptors of the RAR (retinoic acid receptor) and RXR (retinoic acid X receptor) type. The known ligand of RAR receptors is the trans isomer of the acid form of vitamin A (trans-retinoic acid).

In many cellular types, including epithelial cells, ROL is metabolized into retinyl esters.

The importance of retinoids in dermatology goes back to the first observations in animals of cutaneous abnormalities induced by a deficiency in vitamin A (Wolbach et al., *J. exp. Med.* 43: 753).

Today, a large number of retinoids have been synthesized. The main fields of use remain dermatological indications such as actinic keratoses, acne and generally topical or oral treatment of keratinization disorders such as psoriasis and Darier's disease.

Moreover, a certain number of combinations or associations with retinoids are known:
  combinations of molecules acting on cellular differentiation and immunomodulation, for example a combination of retinoids and chemotherapy in cutaneous lymphomas (Thestrup-Petersen et al., *Br. J. Dermatol.* 118: 811-818),
  combination of retinoids and phototherapy for example in association with psoralenes (Saurat et al., *Dermatologica* 177: 218-224),
  combination of molecules affecting the metabolism of retinoids. This is for example the case of the interaction between azoles and derivatives of vitamin D inhibiting the metabolism of retinoids and allowing the intracellular rates of active hormone to be increased (Kato et al., *Biochem. J.* (1992) 286: 755-760, Jugert et al., *Skin Pharmacol.* 1998).

Moreover it is known that one of the major secondary effects of retinoids during a topical application remains induced irritation. This effect may be redhibitory to observing the treatment.

Retinaldehyde (RAL), a member of the family of retinoids, is a natural metabolite of vitamin A, presently used in topical application in humans. It was demonstrated that RAL exerts biological activity in the skin by inducing epidermal hyperplasia, as well as a clear increase in the expression of CD44 and of HA in the follicular and interfollicular epidermis of C57BL/6 and hairless SKH1 mice (hairless SKH1). These effects have also been observed as a result of topical application of retinoic acid (RA) and of retinol (ROL). However, the expression of CD44 and that of HA have been more strongly increased in mice treated with RAL than in those treated with RA or ROL.

CD44 is a polymorphic transmembrane glycoprotein which has several isoforms generated by alternative splicing and post-translational modifications. In a recent study, we demonstrated that two major functions of CD44 in murine skin are (i) regulation of keratinocyte proliferation in response to extracellular stimuli and (ii) the maintaining of local homeostasis of HA (Kaya G., Rodriguez I., Jorcano J L., Vassalli P., Stamenkovic I. *Selective suppression of CD44 transgene driven by a tissue-specific promoter disrupts hyaluronate metabolism in the skin and impairs keratinocyte proliferation. Genes & Development.* 11(8): 996-1007, 1997). We have also observed a reduction in the expression of epidermal CD44 in patients suffering from sclero-atrophic lichen, which is potentially responsible for dermal deposition of HA and epidermal atrophy in this disease (Kaya G., Augsburger E., Stamenkovic K., Saurat J H. *Decrease in epidermal CD44 expression as a potential mechanism for abnormal hyaluronate accumulation in superficial dermis in lichen sclerosus and atrophicus. Journal of Investigate Dermatology.* 115(6): 1054-8, 2000).

CD44 is involved in cell-cell interactions and cell-matrix interactions. A recent study shows that the pair formed by CD44 and HA fragments (CD44-HAF) is an inducer of mitoses and of HA neosynthesis (Laurent T C, Laurent U B, Fraser J R. *The structure and function of hyaluronan: An overview. Immunol. Cell Biol.* 74(2): 1-7, 1996). The epidermal and dermal effects of HA and RAL therefore seem to be mediated by CD44.

Presently, there are pharmaceutical and cosmetic preparations containing inorganic salts of high molecular weight HA, notably Healon, Hyalgan, Provisc, Vitrax and those cited in Martindale The Complete Drug reference, 32nd edition, 1999, The Pharmaceutical Press Editor.

However, HA has difficulty in crossing the skin given its high molecular weight.

This is why, in International Application WO 02/076470A1, the authors propose a composition associating N-acetyl-glucosamine with a retinoid. With this combination, the synthesis of hyaluronic acid may be synergically increased by epidermal cells in vitro. No obtained results after applying the formulation in vivo are mentioned.

Japanese Application 11279042 describes compositions based on sulfated hyaluronic acid fragments, said fragments preferably having a molecular weight between 1,000 and 50,000 Da, the sulfate groups occupying 10 to 90% of the whole of the substituents R1, R2, R3 and R4 in the formula. These low molecular weight fragments are very active for maintaining elasticity of the skin and avoiding keratinization. On the contrary, non-sulfated hyaluronic acid fragments proved to be inactive in the test.

Now, the inventors have surprisingly shown that non-sulfated HA hydrolyzed into fragments with molecular weight between 50,000 and 750,000 Da have a biological activity on the skin which is amplified when these fragments are associated with a retinoid.

Accordingly, the present invention relates to compositions intended for topical application, characterized in that they comprise as an active ingredient, one or more hyaluronate fragments of low molecular weight between 50,000 and 750,000 Da.

In a preferred embodiment of the invention, the molecular weight of hyaluronate fragments is between 50,000 and 250,000 Da or between 250,000 and 750,000 Da.

In another preferred embodiment of the invention, the compositions further contain at least one retinoid.

The combination of hyaluronate fragments with a molecular weight between 50,000 and 750,000 Da with a retinoid has a synergic effect on the synthesis of hyaluronic acid by keratinocytes.

In the sense of the present invention, by retinoid is meant retinol and its isomers, retinol, retinoic acid, and its isomers and the esters of retinoid acid.

By hyaluronate is meant any salt, notably sodium hyaluronate.

The topical compositions according to the invention may also contain dyes, silicone oils, retinoids, or colour pigments, antiseptics, vegetable oils, anti-oxidizing agents, mineral salts, thickeners, pH modifiers, agents absorbing ultraviolet rays, vitamins or any other pharmaceutically and dermatologically acceptable excipient.

The compositions according to the invention may be used in cosmetology and in dermatology for preventing or improving wrinkled skins, dry skins . . . and the firmness and humidity of the skin may be upheld with them.

The compositions according to the invention may be used in topical preparations, in the field of dermatology or cosmetology, with the purpose of preventing or treating dermatoses associated with atrophy of the cutaneous tissue and for which it will be necessary to improve the state of moistening of the skin, to reduce cutaneous atrophy as for example in the secondary effect of corticoid treatments, to reduce wrinkles, to combat cutaneous aging whether photo-induced or not, to re-initiate epidermal and dermal cell activity, to tone up the skin, to increase its elasticity.

The invention is illustrated by the examples and figures which follow.

FIG. 1 illustrates the amount of HA measured in the epidermis in non-treated animals or in animals treated twice daily by preparation 5, preparation 3 or preparation 7, obtained according to the operating procedures described in Examples 1 and 2.

FIG. 2 illustrates the dosage of HA in the dermis in non-treated animals or treated with preparation 5, 3 or 7, as prepared in Examples 1 and 2.

EXAMPLE 1

Effect of Topically used Hyaluronate Fragments

1. Materials and Methods
1.1. Preparations
3 types of hyaluronate fragments (HAF) were evaluated:
very high molecular weight HAF (1,000,000-2,000,000 Da)

low molecular weight HAF (50,000-750,000 Da)
   HAF (250,000-750,000 Da)
   HAF (50,000-250,000 Da)
very low molecular weight HAF (1,000-20,000 Da)

These fragments were included in standard cosmetic preparations, two exemplary compositions of which are given in the table 1 hereafter:

| Ingredients | Amounts in % | Amounts in % |
|---|---|---|
| PEG 600 | 5 | — |
| PEG 400 | — | 1 |
| Sorbitol | — | 2 |
| Glycerin | — | 10 |
| BHT | 0.02 | — |
| Sodium lauryl sulfate | — | 0.25 |
| Carbopol | 1 | — |
| Vitamin E acetate | 0.5 | — |
| Spermaceti | — | 6 |
| Keto stearly alcohol | — | 3 |
| Thick vaseline oil | 5 | — |
| Cremophor RH 40 | 2 | — |
| Sorbic acid | 0.05 | — |
| Nipagin | 0.15 | — |
| Phenonip | — | 1 |
| Triethanolamine | 2,48 | — |
| Water | qsp 100 | qsp 100 |

1.2. Measurement of the Activity of HAFs

Hairless SKH1 mice are used with 3 animals per group.
The different preparations are applied topically.
The epidermal thickness is measured with a graduated eyepiece (Zeiss); magnification 40 times, it is averaged over 5 fields per mouse.
Dermal cellularity is evaluated by calculating the number of dermal cells, magnification 40 times, it is averaged over 5 fields per mouse.
The number of proliferative cells of the epidermis and of the dermis is revealed by immunomarking Ki 67 with an anti Ki-67 antibody (anti-mouse rat, Dako).
The presence of hyaluronate in the dermis is measured after applying different preparations at the rate of two applications daily according to the ELISA technique (Corgenix) and hyaluronate is revealed on histological sections stained by colloidal iron.

2. Results
2.1. Effects on Epidermal Thickness, Dermal Cellularity and the Number of Proliferative Cells The results are grouped in Tables 2 and 3.
Preparations 2 and 3 formulated with low molecular weight HAFs according to the invention and applied topically, significantly increase the epidermal thickness and dermal cellularity in hairless SKH1 mice, as compared with preparations 1 and 4 containing high and very low molecular weight HAFs, respectively (Table 2). Preparation 3 also significantly increases the number of proliferative cells of the epidermis and dermis in hairless SKH1 mice, as compared with preparations 1 and 4 (Table 3).

Topical application of preparations 2 and 3 induces increased cellularity in the surface and deep dermis. The cells which are increased in number are mainly fibroblasts which have an activation phenotype with a very developed endoplasmic reticulum.

2.2. Effects on the HA Level in the Dermis

The results are grouped in Table 4.
The presence of HA in the dermis was detected for preparations 2 and 3 (preparation 3>preparation 2). The HA level is not detectable after applying preparations 1 and 4.

Thus, the inventors have shown that topical application of low molecular weight HAF has two major consequences:

1—Significant epidermal hyperplasia accompanied by an increase in cell proliferation.

2—Focal accumulation of HA in the surface dermis with significant increase in the number of fibroblasts, consequences which are not observed with high and very low molecular weight HAFs.

EXAMPLE 2

Effect of the Association of a Retinoid with Low Molecular Weight HAFs

1. Materials and Methods

The fragments from Table 5 are included in standard cosmetic preparations as exemplified earlier.

2. Results

They are grouped in Tables 6 and 7 and in FIGS. 1 and 2.
Topical application of preparations 6 and 7 increase the number of thickened epidermis foci.

The effect of application of RAL alone (preparation 5) is comparable to the effect obtained with preparation 8 associating HAF of small molecular size with RAL, proof that there is no synergy between RAL and very low molecular weight fragments.

The synergic effect of the HAF-RAL association is particularly visible as the level of dermal cellularity for preparations 6 and 7 (cf. Table 5).

Topical application of preparations 6 and 7 also increases staining of dermal HA (preparation 7>preparation 6) (cf. Table 7).

TABLE 1

HAF-based preparations

| Type of fragment | Preparation 1 | Preparation 2 | Preparation 3 | Preparation 4 |
|---|---|---|---|---|
| HAF (1,000,000-2,000,000 Da) | 0.2% | — | — | — |
| HAF (250,000-750,000 Da) | — | 1% | — | — |
| HAF (50,000-250,000 Da) | — | — | 0.2% | — |
| HAF (1,000-20,000 Da) | — | — | — | 0.2% |

TABLE 2

Effects of the HAFS according to the invention (1)

| Preparation | Epidermal thickness (mm) | Dermal cellularity (c/fields) |
|---|---|---|
| Controls | 0.07 ± 0.02 | 96 ± 8 |
| Preparation 1 | 0.14 ± 0.02 | 99 ± 2 |
| Preparation 2 | 0.17 ± 0.01 | 193 ± 4 |
| Preparation 3 | 0.32 ± 0.06 | 257 ± 6 |
| Preparation 4 | 0.11 ± 0.02 | 99 ± 4 |

TABLE 3

Effects of the HAFS according to the invention (2)

| Preparation | Edidermal Ki 67 (c/fields) | Dermal Ki 67 (c/fields) |
|---|---|---|
| Controls | 26 ± 1 | 0.95 ± 0.6 |
| Preparation 1 | 28 ± 4 | 1 ± 0.2 |
| Preparation 2 | ND* | ND |
| Preparation 3 | 96 ± 9 | 5 ± 1 |
| Preparation 4 | 27 ± 1 | 1 ± 0.3 |

*ND: Not determined

TABLE 4

Effects of the HAFS according to the invention on the presence of HA in the dermis

| Preparation | Presence of HA in the dermis revealed by staining with colloidal iron. |
|---|---|
| Controls | – |
| Preparation 1 | – |
| Preparation 2 | ++++ |
| Preparation 3 | +++++ |
| Preparation 4 | – |

TABLE 5

Préparation based on HAF and retinoids.

| Fragments | Preparation 5 | Preparation 6 | Preparation 7 | Preparation 8 |
|---|---|---|---|---|
| HAF (250,000-750,000 Da) | — | 1% | — | — |
| HAF (50,000-250,000 Da) | — | — | 0.2% | — |
| HAF (1,000-20,000 Da) | — | — | — | 0.2% |
| Retinaldehyde(RAL) | 0.05% | 0.05% | 0.05% | 0.05% |

TABLE 6

Study of the synergic effect of HAFs and RAL on epidermal thickness and dermal cellularity

| Preparation | Epaisseur épidermique (mm) | Cellularité dermique (c/champs) |
|---|---|---|
| Contrôles | 0.07 ± 0.02 | 96 ± 8 |
| Preparation 5 | 0.17 ± 0.02 | 98 ± 4 |
| Preparation 6 | 0.17 ± 0.04 | 195 ± 3 |
| Preparation 7 | 0.33 ± 0.01 | 258 ± 5 |
| Preparation 8 | 0.19 ± 0.02 | 97,6 ± 1 |

TABLE 7

Detection of the presence of HA in the dermis after applying HAF-RAL

| Preparation | Presence of HA in the dermis revealed by staining with colloidal iron. |
|---|---|
| Controls | – |
| Preparation 5 | – |
| Preparation 6 | +++++ |
| Preparation 7 | ++++++ |
| Preparation 8 | – |

The synergic effect of the HAF-RAL association was also revealed by ELISA dosage of the presence of HA in the dermis and epidermis of mice which were treated with the different preparations mentioned above.

The results show a significant increase in the production of HA both in the dermis (FIG. 2) and in the epidermis (FIG. 1) after treatment with the HAF-RAL association (preparation 7) comparatively to the treatment with RAL alone (preparation 5) or HAF alone (preparation 3).

What is claimed is:

1. Topical compositions, comprising as an active ingredient, one or more hyaluronate fragments, wherein the hyaluronate fragments all have a molecular weight of between 50,000 and 750,000 Da and retinal.

2. The compositions according to claim 1, wherein the molecular weight of the hyaluronate fragments is between 50,000 and 250,000 Da.

3. A cosmetic method for improving wrinkled or dry skins comprising the topical application of a composition according to claim 1.

4. A cosmetic method for treating dermatoses associated with atrophy of the cutaneous tissue comprising the topical application of a composition according to claim 1.

5. A dermatological method for improving or treating wrinkled or dry skins comprising the topical application of a composition according to claim 1.

6. Method of treatment for treating dermatoses associated with atrophy of the cutaneous tissue comprising the topical application of a composition according to claim 1.

7. The compositions according to claim 1, wherein the molecular weight of the hyaluronate fragments is between 250,000 and 750,000 Da.

* * * * *